United States Patent [19]
Awad, Jr.

[11] Patent Number: 5,110,914
[45] Date of Patent: May 5, 1992

[54] METHOD OF SEPARATING PROTEINS

[75] Inventor: William M. Awad, Jr., Miami, Fla.

[73] Assignee: University of Miami, Miami, Fla.

[21] Appl. No.: 416,299

[22] Filed: Oct. 3, 1989

Related U.S. Application Data

[63] Continuation-in-part of Ser. No. 276,924, Nov. 28, 1988.

[51] Int. Cl.$^5$ .................................................. C07K 3/22
[52] U.S. Cl. .................................. 530/416; 530/399; 530/412
[58] Field of Search ..................... 530/416, 399, 412

[56] References Cited

PUBLICATIONS

Awad, William M., Ph.D., M.D., [Abstract] "New General Techniques for Protein Separation", *Innovation '89 Technology Transfer in Florida*, presented by Gold Coast Venture Capital Club, University of Miami Venture Council Forum, Apr. 6, 1989.

Alpert et al. Preparation of a Porous Microparticulate Anion-Exchange Chromatography Support for Proteins, Journal of Chromatography, vol. 185, 1979, pp. 375-392.

Furuya et al. Electrostatic and hydrophobic effects in chromatography of Rabbit IgC Immunoglobulins on Aminohexyl Sepharose Substituted with bis(p-chlorophenyl)-acetic acid, Chemical Abstracts, vol. 100, No. 13, Mar. 26, 1984, p. 481, Abstract No. 101314u.

J. Lam, Separation and Protection of Gamma-electron-rich Compounds on Caffeine-impregnated Silica Gel Layers, Chemical Abstracts, vol. 80, No. 3, Jan. 21, 1974, p. 417, Abstract No. 14770q.

P. M. Reuben, Protein Chromatography Based upon Combined Pi-electron and Electrostatic Interactions, Chemical Abstracts, vol. 112, No. 21, May 21, 1990, p. 357, Abstract No. 194681x.

Primary Examiner—Richard L. Raymond
Assistant Examiner—Shailendra Kumar
Attorney, Agent, or Firm—Cushman, Darby & Cushman

[57] ABSTRACT

A method for separating organic compounds, specifically proteins, is provided. The method for separating organic compounds is based on a combined pi-electron and electrostatic interaction of the exchanger with specific components of the organic compound. The method provides both an anionic and cationic exchanger. Each exchanger can provide more than one dimension of separation.

17 Claims, 13 Drawing Sheets

FIG. IIA
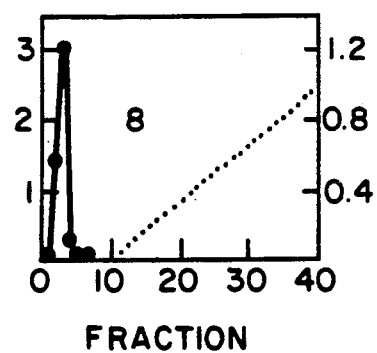
FIG. IIB
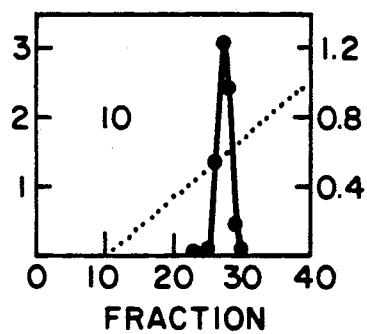
FIG. IIC
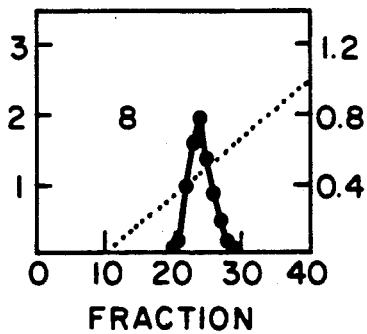
FIG. IID
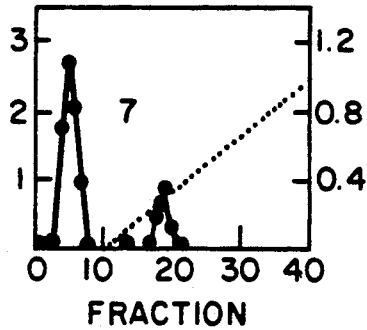
FIG. IIE
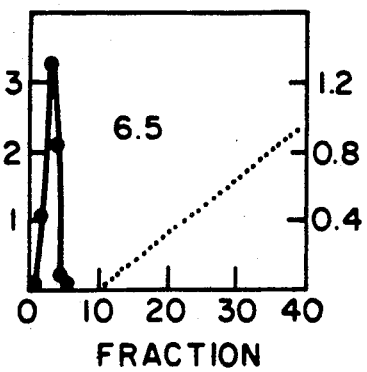

METHOD OF SEPARATING PROTEINS

This is a continuation-in-part application of application Ser. No. 07/276,924 filed Nov. 28, 1988.

BACKGROUND OF THE INVENTION

This is a continuation-in-part application of application Ser. No. 07/276,924 filed Nov. 28, 1988.

The present invention relates generally to methods of separating organic compounds. More specifically, the present invention relates to a method of separating proteins.

In many industries, it is desirable to separate proteins. For example, in research, it is necessary to separate proteins in order to determine whether a given component is providing certain characteristics or results. In other industries, such as pharmaceuticals, food industries, and cosmetics, it is necessary to separate proteins in order to provide certain products or improve products. Furthermore, it may be desirable to separate proteins as a diagnostic tool or treatment. However, there are a variety of other reasons and needs for separating proteins.

There are a variety of methods for separating proteins. Separation can be based on: molecular size; solubility; electric charge; differences in absorption characteristics; and biological affinity for other molecules. Examples of such methods include: ion exchange; gel filtration; hydrophobic chromatography; and specific chromatographies by use of monoclonal antibodies. Ion exchange functions to separate proteins by charge, while gel filtration functions to separate the proteins by weight and shape. Two commonly used materials for ion exchange chromatography are: diethylaminoethyl-cellulose (DEAE-cellulose); and carboxymethylcellulose (CM-cellulose). DEAE-cellulose contains positively charged groups at pH 7.0 and is therefore an anion exchanger. CM-cellulose contains negatively charged groups at neutral pH and is a cation exchanger.

Although, by utilizing the presently available methods, it is possible to separate and purify many proteins, current methods, even when combined, still are not sufficient to resolve all proteins. In this regard, the properties of some related amino acid residues in proteins cannot be individuated by presently available techniques. For example, the inventor of the present invention does not know of a technique that separates proteins on the basis of differences in arginine and lysine ratios except by chromatography at very high pH values wherein denaturation can be expected. Furthermore, the available techniques are not able to separate certain proteins, in certain applications, so as to yield a sufficiently pure product.

There is therefore a need for further methods of separating proteins.

SUMMARY OF THE INVENTION

The present invention provides new methods for separating organic compounds, specifically proteins. To this end, the present invention provides a method for separating organic compounds, specifically proteins, based on a combined pi-electron and electrostatic interaction of the exchanger with specific components of the organic compound. Specifically, the present invention provides a method of separating proteins based on a combined pi-electron and electrostatic interaction of the exchanger with specific amino acids residues of proteins and polypeptides.

In an embodiment of the present invention, the exchanger is anionic. This exchanger functions to separate proteins based on amino acid residues that have a positive charge and include pi electrons. In a preferred embodiment, the exchanger includes a barbiturate, containing a ligand that has a high affinity for the guanidino group of arginine (and homoarginine) and for the imidazole group of histidine. Due to the pKa value of histidine, the barbiturate ligand provides a means for separating proteins at two separate pH ranges. It has been found that proteins will separate primarily on the basis of their arginine contents at pH values of 8 or greater and on the basis, primarily, of the sums of their arginine and histidine contents at pH values of approximately 7 or lower. Thus, cationic proteins can take advantage of this matrix at different pH levels for two different kinds of separation.

In an embodiment, the anionic exchanger can include a ligand having a focussed charge or a spread out charge. This provides a second dimension to the anionic exchanger allowing further separation. For example, an anionic ligand can be selected wherein the pi electron distribution is similar to that of the barbiturate ring, but because of fewer electro-negative atoms, the charge is more focussed. An example of such a ligand would be tyramine coupled by its amino group to a neutral matrix. The pKa of the phenolic group can be reduced with only a modest effect on the electrostatic effect by adding electron-withdrawing groups at both positions ortho to the phenolic hydroxyl group.

Furthermore, the anionic exchanger can provide a third dimension of separation. This third dimension is provided by the anionic exchanger by modifying the leash length or the leash structure of the exchanger. Because of the restrictive geometry of the combined pi-electron and electrostatic reaction, variations in leash length will contribute to different accessibilities to individual amino acid residues in a protein.

In an embodiment, the anionic exchanger includes paranitrophenol.

In another embodiment of the present invention, the exchanger is cationic and functions to separate proteins having amino acid residues that are negatively charged and have pi electrons Specifically, the cationic exchanger will separate proteins on the basis of an affinity for tyrosine residues in addition to the expected simple electrostatic affinities for the carboxyl residues of aspartate and glutamate residues. An example of the exchanger is N($\beta$-guanidinoethyl)carbamylmethylcellulose (GECM-cellulose). Similar to the cation exchanger, a second dimension can be introduced with positively charged matrices with expanded pi-electron groups and a greater dispersal of electro-negative atoms which have an equal or higher affinity for tyrosine residues and a lower affinity for aspartate and glutamate residues than that demonstrated by GECM-cellulose. Examples of these ligands include N($\beta$-biguanidoethyl)- or N($\beta$-isomelaminoethyl)-carbamylmethyl-celluloses.

In an embodiment, the anion exchanger provides a third dimension by varying the leash length and/or structure.

In an embodiment, an anion exchanger is provided having the structure:

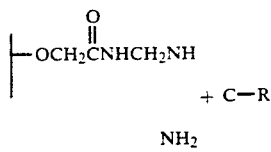

wherein R is alkane. In an embodiment R is methyl.

The exchanger of the present invention can be used in columns to separate proteins In an embodiment, the ligands of the present invention are attached to a matrix that can include, inter alia: cellulose; agarose; dextran; acrylamide; supocel; silica gels; polystyrene; starch; and glass.

Additional features and advantages of the present invention will be apparent from the detailed description of the presently preferred embodiments and from the drawings.

DETAILED DESCRIPTION OF THE PRESENTLY PREFERRED EMBODIMENTS

Figure 1:
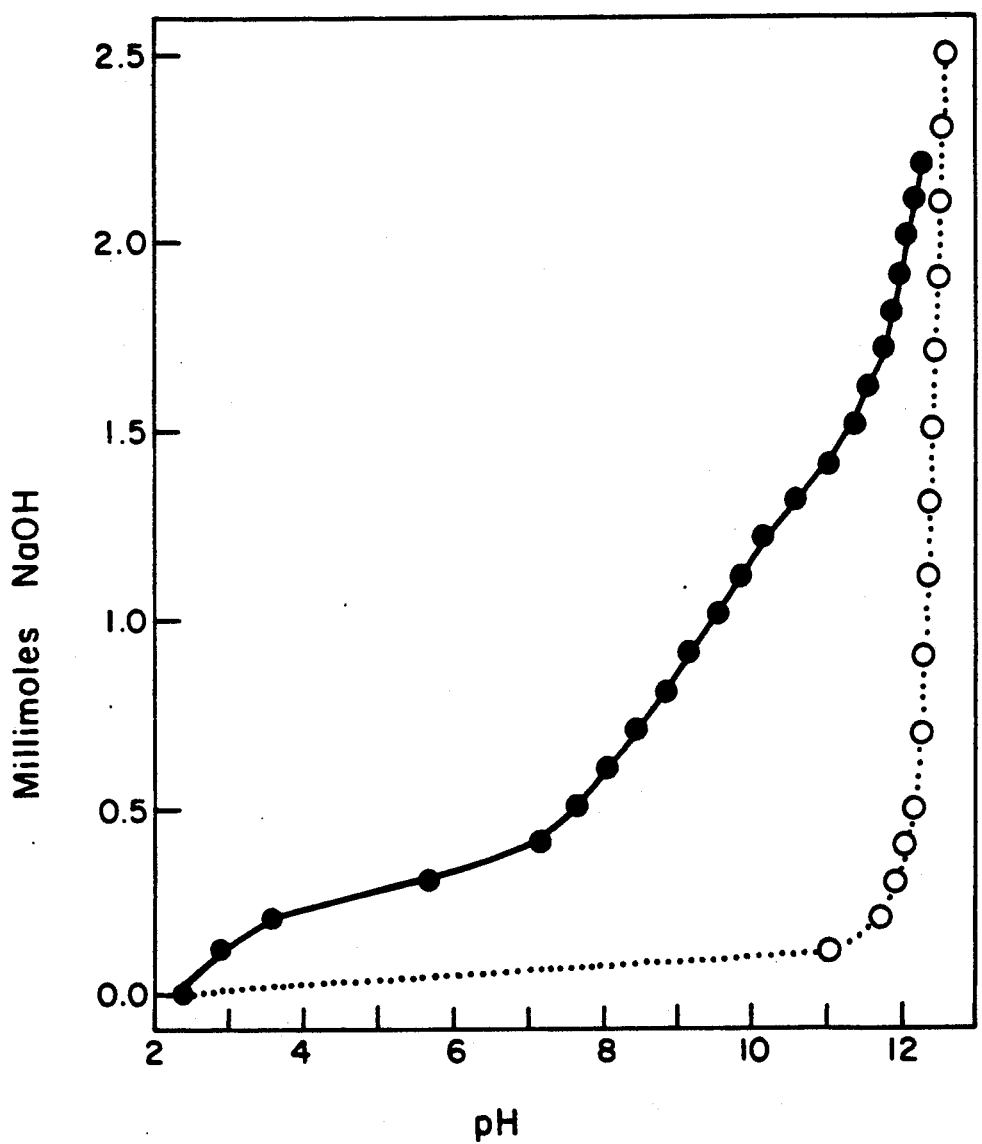
FIG. 1 illustrates a graph of titration of covalently inked barbiturate to a Sepharose matrix.
Figure 2C:
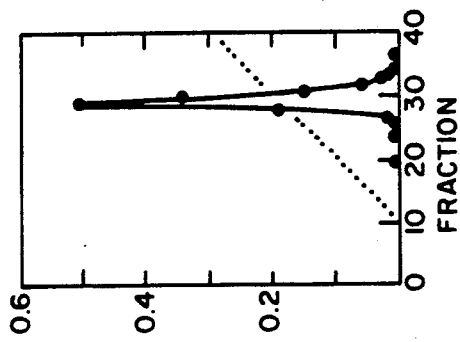
FIG. 2(A-E) illustrates the chromatography results of pairs of proteins using CM-cellulose or DEAE-cellulose. Y axis-$A_{280}$●—●, and M NaCl FIG. 3(A-C) illustrates the separation of a native and a guanidinated protein when passed through a barbiturate derived Sepharose matrix of the present invention. Y axis-$A_{280}$●—●, and M NaCl FIG. 4(A-C) illustrates the separation of a native and a guanidinated protein when passed through a barbiturate derived ,Sepharose matrix of the present invention. Y axis-$A_{280}$●—●, and M NaCl FIG. 5(A-C) illustrates the separation of a native and a guanidinated protein when passed through a barbiturate derived Sepharose matrix of the present invention. Y axis-$A_{280}$●—●, and M NaCl FIG. 6(A-C) illustrates the separation of a native and a guanidinated protein when passed through a barbiturate derived Sepharose matrix of the present invention. Y axis-$A_{280}$●—●, and M NaCl FIG. 7(A-C) illustrates the separation of porcine elastase from bovine chymotrypsinogen. Y axis-$A_{280}$●—●, and M NaCl FIG. 8(A-F) illustrates the chromatography results at a pH of 8.5 and 6.5 with detection of amino groups by reaction with fluorescamine. Relative Fluorescence $A_{280}$●—●, and M NaCl FIG. 9(A-B) illustrates the elution patterns of tyramine through GECM-cellulose. Y axis-$A_{280}$●—●, and M NaCl FIG. 10(A-B) illustrates the elution patterns of phenylacetic acid through DEAE-cellulose and GECM-cellulose. Y axis-$A_{280}$●—●, and M NaCl FIG. 11(A-E) illustrates the elution patterns for N-acetyltyramine through DEAE-cellulose and ECM-cellulose. Y axis-$A_{280}$●—●, and M NaCl FIG. 12(A-D) illustrates the elution patterns for chymotrypsinogen-A, ribonuclease, bovine serum albumin, and ovalbumin through matrices of DE-52, CM-52, and GECM-cellulose. Y axis-$A_{280}$●—●, M NaCl
Figure 2B:
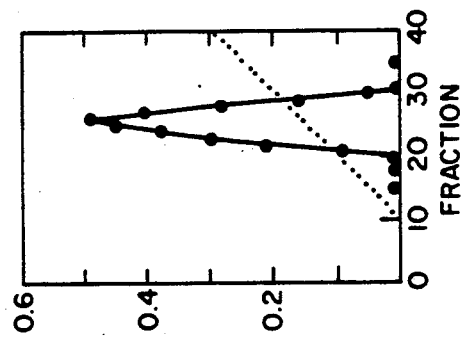
Figure 2A:
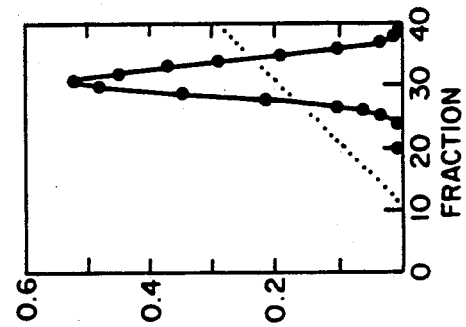
Figure 2E:
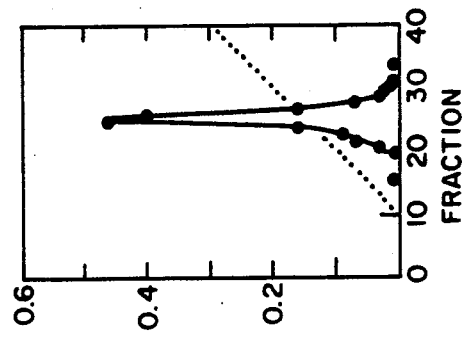
Figure 2D:
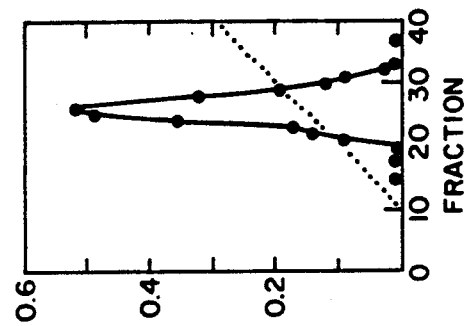

The present invention provides a new technique for the separation of organic compounds. More specifically, the present invention provides a new technique for protein purification. The technique is based on a method of separating proteins based on a combined pi-electron and electrostatic interaction of the exchanger with specific amino acid residues of the proteins and polypeptides. The present invention is specifically directed to the separation of proteins based on amino acid residues on the basis of the pi electrons and electrostatic charges in their side groups. These amino acid residues include arginine and histidine that have positive charges and tyrosine that has a negative charge. The present invention, in an embodiment, also allows the separation of proteins based on the aspartic acid and glutamic acid residues.

The present invention provides an exchanger that can be cationic or anionic. As set forth in detail below, by varying or focussing the charge on the ligand, it is possible to provide a second dimension for protein separation with the exchangers. By varying the leash length and/or the leash components, it is also possible to provide a third dimension for separating proteins.

The inventor of the present invention has found a method of separating proteins, based on amino acid residues in the proteins, on the basis of pi electrons and electrostatic charges in the side groups of the amino acid residues. Pursuant to the methods of the present invention, the present invention can separate at least four sets of amino acid residues based on their pi electrons and electrostatic charges. These amino acid residues (or sets) are: arginine; arginine and histidine; tyrosine; and aspartic acid and glutamic acid. It should be noted that aspartic acid and glutamic acid are separated as a pair. Accordingly, the present invention allows the separation of all the amino acid residues that include pi electrons and are charged at a viable pH. The present invention provides a panel of techniques that provide different separations for proteins than heretofore possible.

In an embodiment of the present invention, the exchanger, or ligand, is a barbiturate ring. Barbiturates are planar molecules except for the groups attached to carbon-5. The large number of electronegative atoms permits a significant dispersion of the negative charge in the presence of a pi-electron system having 3 carbon, 3 oxygen, and 2 nitrogen atoms. However, on the other hand, the planar guanidinium ion has a significant pi electron system with a dispersed net positive charge. Set forth below are such structures:

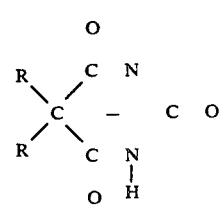

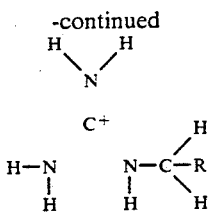

The synthesized barbiturate-containing matrix shows a general high affinity for the guanidino group of arginine (and homoarginine) and for the imidazole group of histidine. Utilizing a barbiturate containing matrix, proteins can be separated primarily on the basis of arginine content at pH values of approximately 8 or higher and on the basis of the sums of arginine and histidine content at pH values of approximately 6.8 or lower. Accordingly, cationic proteins can take advantage of this matrix at two different pH values for two different types of separation. In contrast, most anionic proteins will probably bind and be separable at the lower pH values only, unless there are a significant or sufficient number of arginine residues to bind at pH 8.

The barbiturate group has a pKa value of about 7.9 in the nonliganded state. A barbiturate with a proton on the carbon-5 instead of one of the alkyl groups should have a pKa of between 4.04 and 4.97. This expands substantially the acidic pH range of applicability of this kind of matrix. This is important in that some proteins can only be separated at lower pH values. It is also possible that related ligands can be utilized including the thiobarbiturates.

Other related structures would be the pyrimidines, purines, and hydantoins and their derivatives.

By way of example, and not limitation, experimental procedures utilizing the barbiturate matrix will now be set forth.

The following chemicals and compositions were utilized. Bovine chymotrypsinogen, α-chymotrypsin, ribonuclease, α-lactalbumin and serum albumin and ovalbumin, agmatine, histamine, and porcine elastase obtained from Sigma. Allyl diethyl ethylmalonate, urea, cyanogen bromide, N-acetylethylenediamine, and O-methylisourea obtained from Aldrich. Sodium azide and barbital obtained from Fisher Scientific. Sepharose 4B obtained from Pharmacia. Guanidinium hydrochloride obtained from Schwarz/Mann. Preswollen microgranular CM-and DEAE-cellulose (Whatman CM- and DE-52) obtained from H. Reeve Angel and Company. Fluorescamine (4-phenyl-spiro[furan-2(3H), 1'-phthalan]-3,3'-dione) obtained from Hoffman-LaRoche. All other chemicals set forth below were of the highest purity available.

The guanidination of proteins followed standard procedures. N-Acetyl-ethylenediamine was reacted with O-methylisourea to synthesize 2-acetamidoethylguanidine. The synthesis of 5-ethyl-5-(3-aminopropyl) barbiturate acid hydrochloride was as follows:

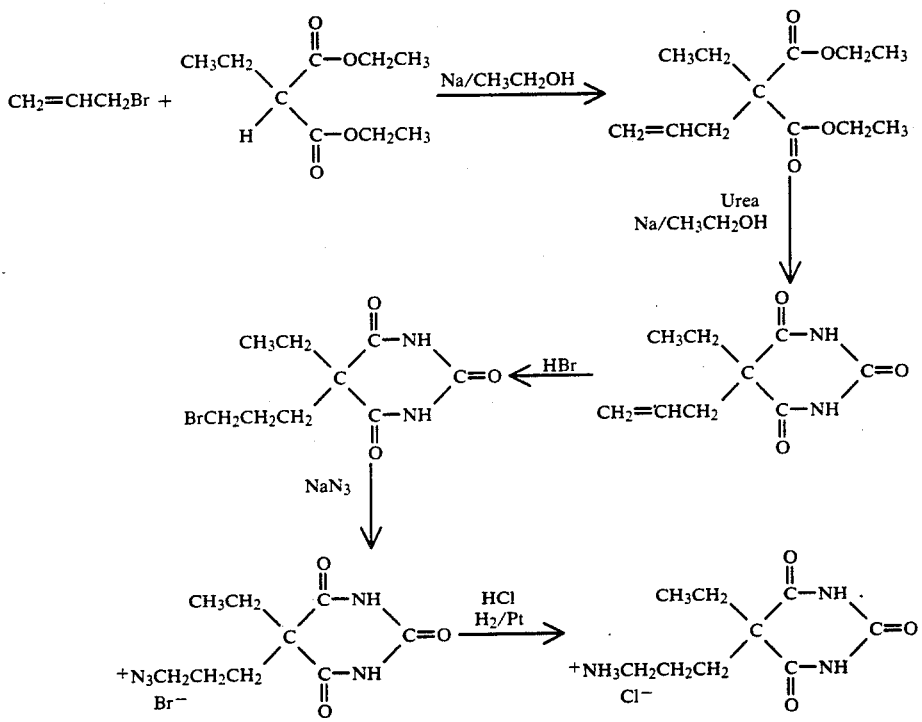

NMR spectra were determined on a Perkin-Elmer FT R-600 spectrometer; all new compounds gave satisfactory proton NMR analyses. Each barbiturate compound showed a single spot after chromatography on precoated thin-layer silica-gel plates (Whatman MK-6F) developed with 1-butanol: ethyl acetate: acetic acid: $H_2O$ (1:1:1:1).

Synthesis of diethyl ethyl allylmalonate

To a solution of 12.2 g of metallic sodium (0.53 moles) in 125 ml of absolute ethanol, which was cooled over ice, was added 100 g of diethyl ethyl allylmalonate (0.53 moles). Following a modest exothermic reaction and a cooling on ice, a slight molar excess of allylbromide (77 g, 0.64 moles) was added. A violent exothermic reaction occurred that last approximately one minute. After the reaction a precipitate formed. Thereafter the reaction mixture was heated to boiling for approximately 2 hours until the solution was neutral as tested by a 1:100 phenothalein:ethanol solution (w/v). The alcohol was then distilled off leaving a solid residue.

500 ml of $H_2O$ was added to the residue and this led to the formation of an oily upper phase and an aqueous lower phase. The oily phase was separated and combined with a 500 ml diethyl ether extract of the aqueous phase. The combined solution was washed successively with water and a saturated aqueous NaCl solution and then treated with solid $MgSO_2O$ for approximately 10 minutes to remove any remaining water. After filtration the anhydrous solution was evaporated to an oily residue which was distilled to yield diethyl ethyl allylmalonate at 95°-100° C./5 mm Hg.

Synthesis of 5-ethyl-5-allylbarbituric acid

Urea (19.76 g, 0.33 moles) was dissolved in a solution of metallic sodium (7.75 g, 0.329 moles) in 170 ml of absolute ethanol. An equimolar amount of diethyl ethyl allylmalonate (75 g, 0.329 moles) was added to the solution, and the combined solution was heated to boiling for more than 5 hours. The solution was cooled to 23° C., neutralized with concentrated HCl, and then filtered. The filtrate was then evaporated to a syrup and 200 ml $H_2O$ was added and made alkaline with NaOH. Thereafter the solution was extracted with ether to remove unreacted diethyl ethylallylmalonate. The aqueous phase was cooled on ice and acidified with cold concentrated HCl. The barbituratic acid derivative separated; it was filtered and dissolved in a minimal amount of ethanol. Water was added until fine crystals began to form; the solution was left overnight at 23° C. The crystals were removed by filtration, washed with cold water, and air dried. The melting point was 157°-159° C.

Synthesis of 5-ethyl-5-(3-bromopropyl)barbituric acid

A suspension of 40 g of 5-ethyl-5-allylbarbituric acid and 800 ml of toluene was stirred and irradiated with a GE sunlamp (275 watts, 110-125 volts) for approximately 90 min. Thereafter, gaseous HBr was passed for 45 min. with further irradiation and stirred for another 45 minutes. The reaction flask was then opened to allow the excess HBr to evaporate. The solution was cooled and filtered. The resulting precipitate was washed with toluene, dried, and then dissolved in a minimal amount of hot acetone. Petroleum ether (60°-68° C.) was added until a small amount of precipitate appeared; the flask was left overnight at 23° C. The crystals were filtered, washed with petroleum ether, and air dried. The melting point was 138°-140° C.

Synthesis of 5-ethyl-5-(3-azidopropyl)barbituric acid

A solution of 30 g of 5-ethyl-5-(3-bromopropyl) barbituric acid and 13 g of sodium azide in 350 ml of acetone was added to 240 ml of water and refluxed for approximately 18 hours. Thereafter, the solution was cooled on ice, filtered, air dried, and dissolved in a minimal amount of hot 95% ethanol. Crystals appeared after cooling and were filtered and air-dried. The melting point was 182°-184° C.

Synthesis of 5-ethyl-5-(3-aminopropyl)barbituric acid hydrochloride

A suspension of 5-ethyl-5-(3-azidopropyl) barbituric acid (20 g) in 160 ml of glacial acetic acid was mixed with 40 m of dimethyoxyethane containing 2 g of platinum oxide and was hydrogenated in a Parr shaker type hydrogenation apparatus at room temperature for approximately 5 hours. The solution was filtered and evaporated to an oil. The oil was dissolved in anhydrous ethanol and saturated with gaseous HCl at approximately 0°-10° C. After the solution was concentrated by evaporation and after the addition of chloroform the hydrochloride salt of the compound came out of solution. This material was redissolved in a minimal amount of methanol and crystallized as chloroform was added. The melting point was 224°-226° C.

Coupling of 5-ethyl-5-(3-aminopropyl)barbituric acid hydrochloride to Sepharose-4B Following a procedure set forth in Cuatrecasas, P. and Anfinsen, C. B. (1971) Methods Enzymol, 22, 345-377, activation with 300 mg of cyanogen bromide per ml of Sepharose-4B was performed at a pH of 10.5. Twenty mg of barbiturate derivative per ml of activated gel was added in 0.1M $NaHCO_3$, pH 9 and placed in a shaker overnight at 4° C. Thereafter, the gel was transferred to 0.2M glycine, pH 8, at 23° C. for approximately 2 hours to block unsubstituted active groups. The gel was then washed with the coupling buffer and 0.1M sodium acetate, pH 4, each containing 0.5M NaCl. A final wash was done with the coupling buffer.

All chromatography set forth below for these experiments was done in columns of 0.8×9 cm. The buffer used was 5 mM sodium phosphate (either pH 8.0 or pH 6.8) unless otherwise indicated. Fractions of 2 ml were collected at a flow rate of one ml/min. After a period of flow with initial buffer each column was eluted with a linear gradient formed with 50 ml each of starting buffer and the same buffer containing either 0.5 or 1M NaCl. Amino acid compositions were analyzed with a JEOL 5AH analyzer using ninhydrin detection after protein samples were hydrolyzed in vacuo in 6M HCl at 110° C. for approximately 22 hours.

FIG. 1 illustrates the broad range of titration of the covalently linked barbiturate to the Sepharose matrix. The titration of 5-ethyl-5-(3-aminopropyl)barbituric acid linked by its amino group to Sepharose 6B (continuous line, solid circles) is compared to the titration of Sepharose 6B (dashed line, open circles). Twenty ml of each matrix was titrated with 0.2 m NaOH. Barbiturates with two alkyl groups attached to carbon-5 have pKa values ranging between 7.45 and 7.99. However, as seen with other charged groups, the matrix expands the range of pKa values. Where there would be a proton instead of one of the alkyl groups attached to carbon-5, pKa values of 4.04 to 4.94 have been recorded; it may be that, in these residues, the hydrogen on carbon-5 is the most acidic proton.

FIG. 2 illustrates the results of chromatography of pairs of proteins utilizing either CM-cellulose or DEAE-cellulose. In panels A through D native proteins were passed with their fully guanidinated derivatives. Two anionic and two cationic proteins were selected. The proteins used were as follows: α-lactalbumin (Panel A); ribonuclease (Panel B); chymotrypsinogen (Panel C); and bovine serum albumin (Panel D). In Panels A and D, DEAE-cellulose was utilized. In Panels B and C, CM-cellulose was utilized.

As indicated, the pairs of proteins emerged as a single peak in each case. Not shown is that elution was continued through 0.5M NaCl in each case without further material appearing which absorbed at 280 nm. The results with panels B and C reemphasizes the fact that guanidino groups do not show a higher affinity for carboxylate groups when compared to primary amino groups.

Panel E shows the elution of a mixture of bovine chymotrypsinogen and porcine elastase, proteins with lysine:arginine ratios of 14:4 and 3:12, respectively, using CM-cellulose. Despite significant differences in arginine and lysine contents, the two proteins coelute, again demonstrating a lack of a significant difference in affinity for carboxylate groups by amino and guanidino residues.

Figure 3A:
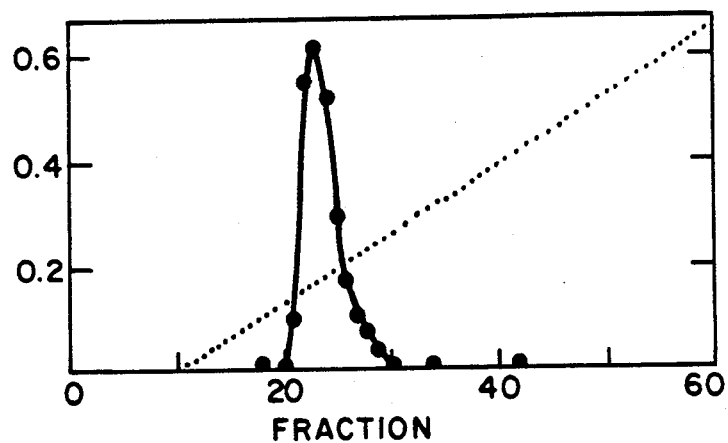
Figure 3B:
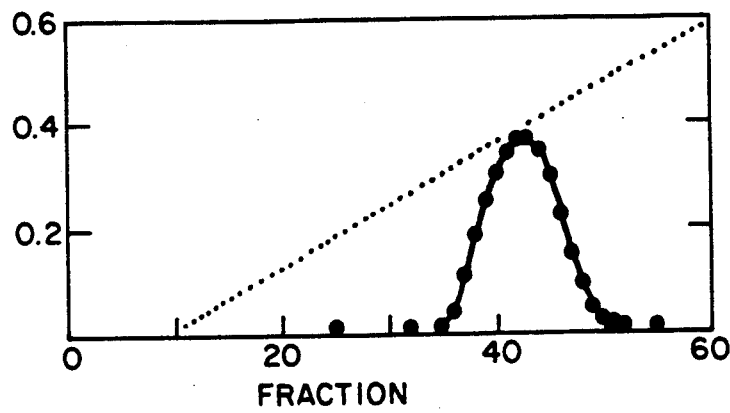
Figure 3C:
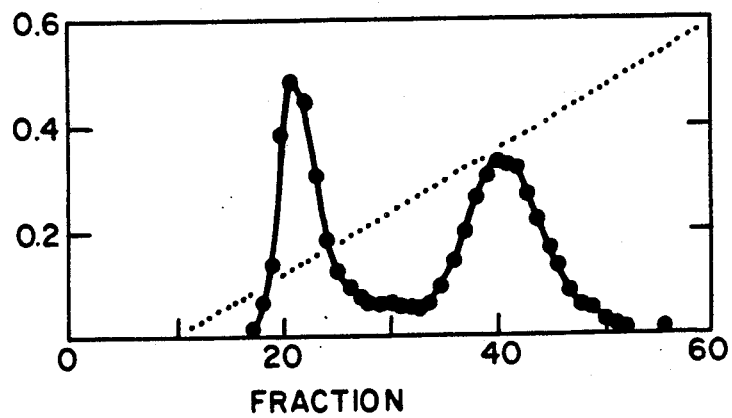
Figure 4A:
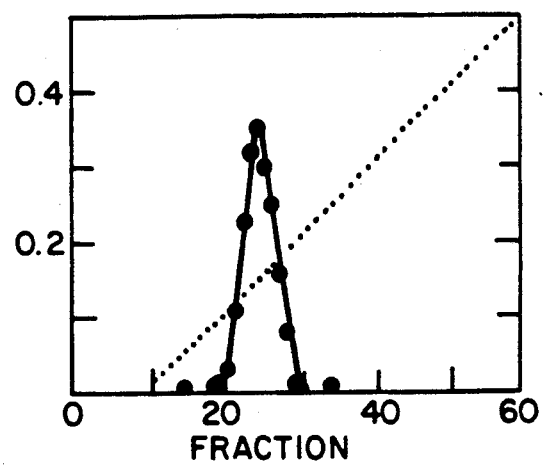
Figure 4B:
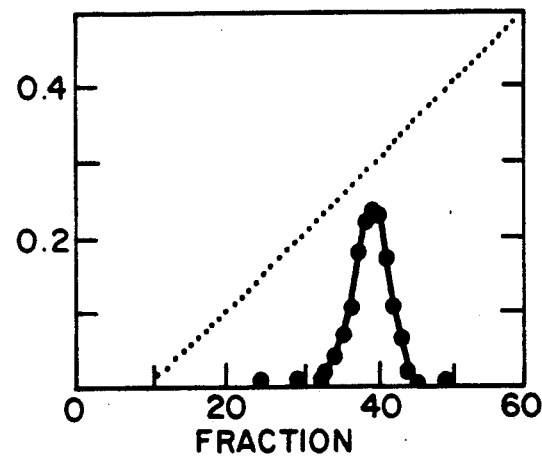
Figure 4C:
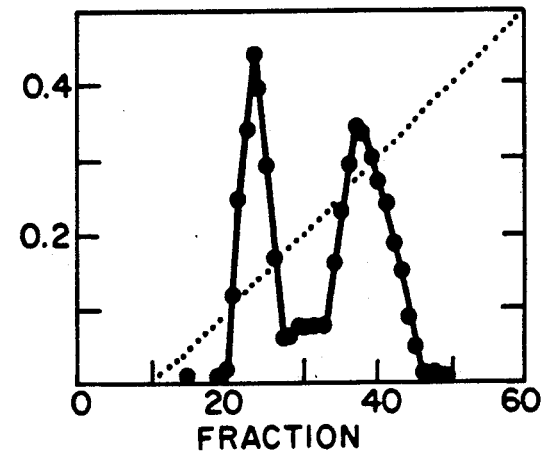
Figure 5A:
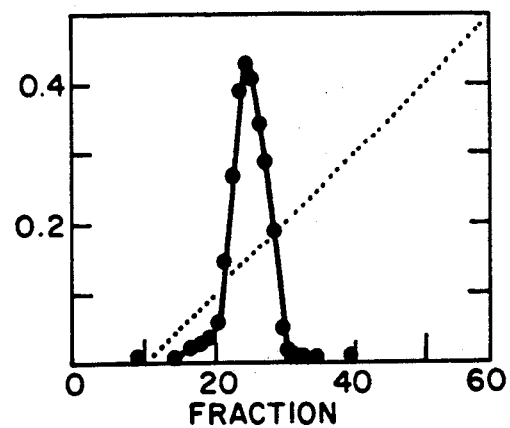
Figure 5B:
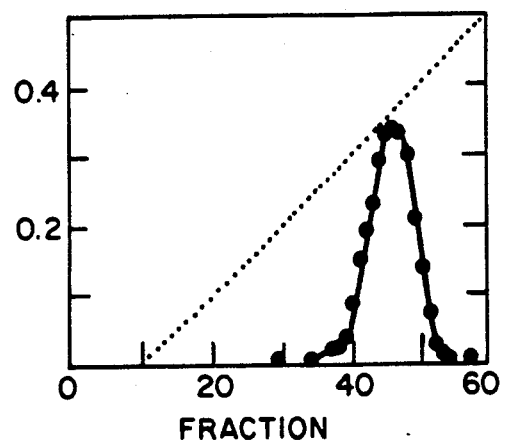
Figure 5C:
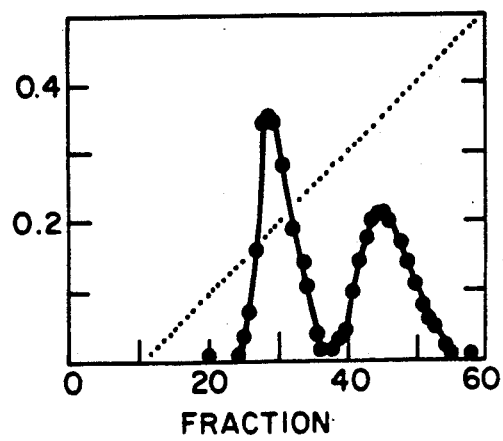
Figure 6A:
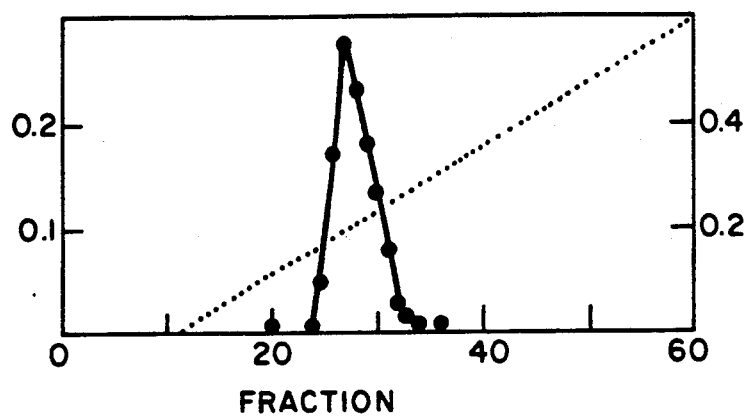
Figure 6B:
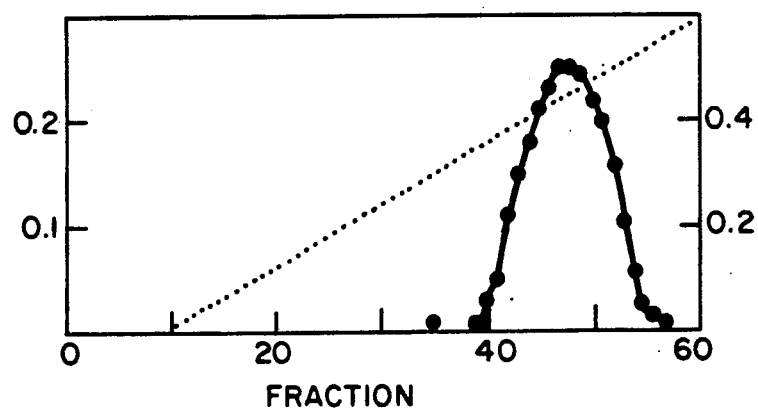
Figure 6C:
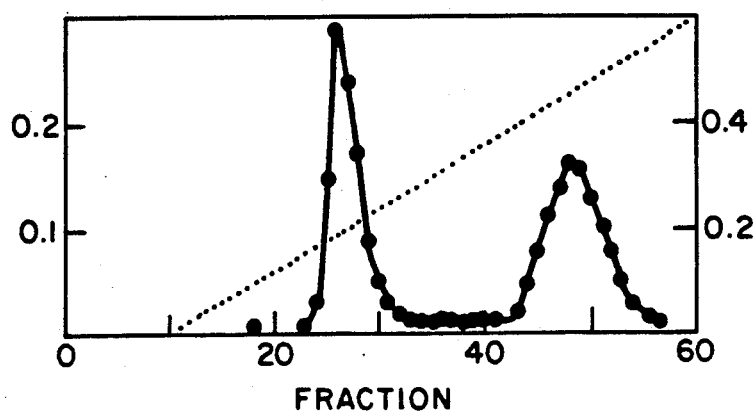

FIGS. 3-6 illustrate the significant separation of guanidinated proteins from native precursors when passed through the barbiturate-derived Sepharose matrix of the present invention. FIG. 3 illustrates chromatography through barbiturate derivative of Sepharose 4B at pH 6.8 of native (panels A and C) and guanidinated (panels B and C) α-lactalbumin. FIG. 4 illustrates chromatography through barbiturate derivative of Sepharose 4B at pH 8 of native (panels A and C) and guanidinated (panels B and C) ribonuclease. FIG. 5 illustrates chromatography through barbiturate derivative of Sepharose 4B at p 8 of native (panels A and C) and guanidinated (panels B and C) chymotrypsinogen. FIG. 6 illustrates chromatography through barbiturate derivative of Sepharose 4B at pH 6.8 of native (panels A and C) and guanidinated (panels B and C) bovine serum albumin.

Table 1 below illustrates the results of the amino acid analyses of the chromatographic components in these fixtures.

which have isoelectric points of 4.8, 5.1, and 4.7, respectively; these proteins do not bind to CM-cellulose.

Figure 7A:
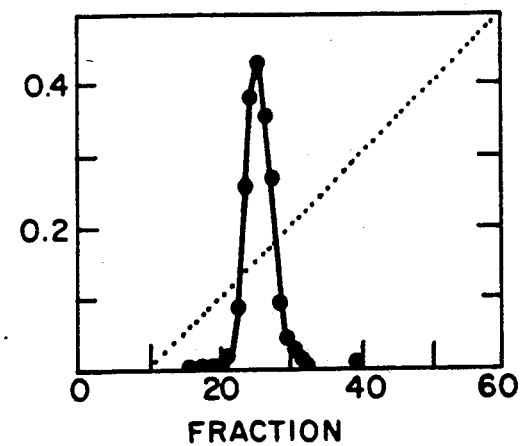
Figure 7B:
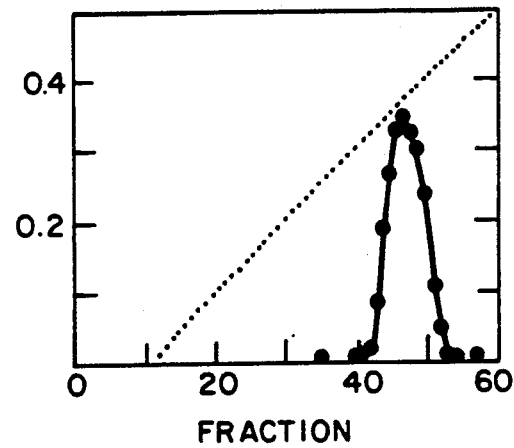
Figure 7C:
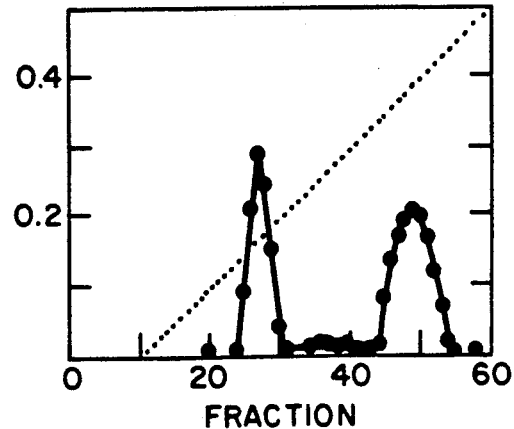
Figure 8A:
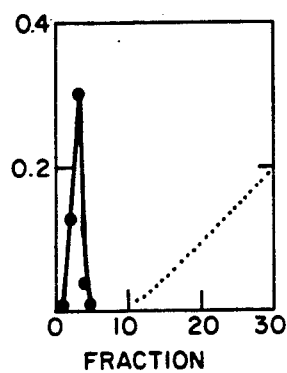
Figure 8B:
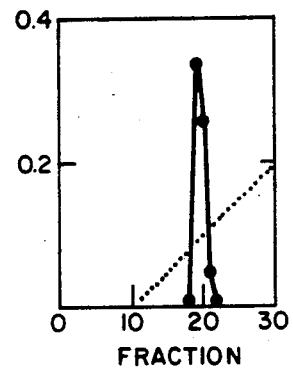
Figure 8C:
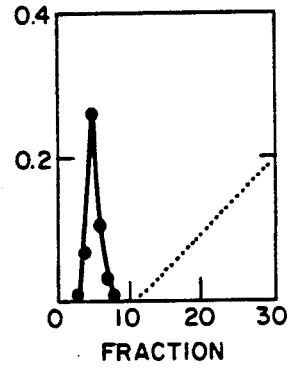
Figure 8D:
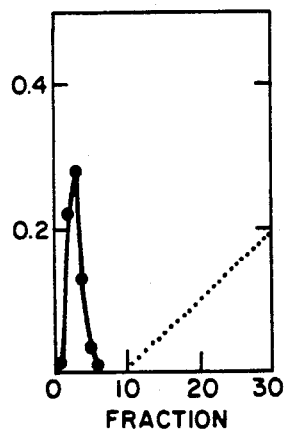
Figure 8E:
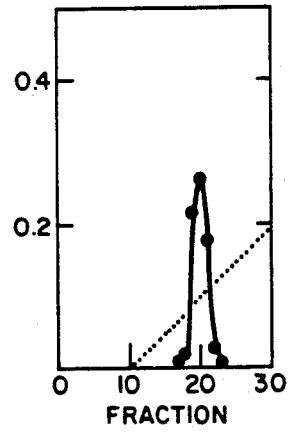
Figure 8F:
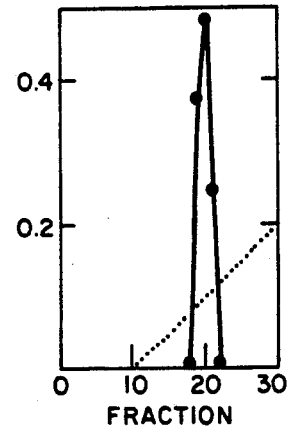

FIG. 7 (see also Table 1) illustrates the complete separation of porcine elastase from bovine chymotrypsinogen. In this regard, the chromatography through barbiturate derivative of Sepharose 4B at pH 8 of native chymotrypsinogen (panels A and C) and native elastase (panels B and C) is illustrated. In contrast to the findings noted in FIG. 2, the elastase with its high arginine content is retarded significantly. These two proteins have similar molecular weights and isoelectric points. These results suggest that the high arginine content of elastase is responsible for the higher affinity of this protein.

In the examples of the three anionic proteins no native component showed binding at pH 8.0 but they did bind at pH 6.8. At pH 6.8 substantial protonation of histidine residues would occur and thereby permit the interaction with the matrix, again based upon a combined pi-electron and electrostatic effect.

An analysis of this aspect required a study of the binding of model compounds. Studies with a mixture of all the common amino acids or with either histidine or arginine alone showed no binding in any instance. Thus, binding was not of a simple electrostatic nature. If the binding occurred via the pi-electron system, the barbiturate group would have to come close to the α-carboxyl groups of amino acids. The ensuing electrostatic repulsion would prevent a pi-electron approximation. To confirm this, agmatine and histidine, the decarboxylated products of arginine and histidine, respectively,

TABLE 1

| Protein | Basic Amino Acid Compositions[a] | | | | | | | | |
|---|---|---|---|---|---|---|---|---|---|
| | Individual Proteins[b] | | | Chromatographed Components[c] | | | | | |
| | | | | First | | | Second | | |
| | Lys | Arg | Har[d] | Lys | Arg | Har | Lys | Arg | Har |
| 1. α-Lactalbumin | | | | | | | | | |
| Native | 12 | 1 | | Not determined | | | Not determined | | |
| Guanidinated | Not determined | | | | | | | | |
| 2. Ribonuclease A | | | | | | | | | |
| Native | 10 | 4 | | 9.7 | 3.8 | 0 | | | |
| Guanidinated | 0.9 | 4.0 | 9.9 | | | | 1.1 | 4.2 | 9.8 |
| 3. α-Chymotrypsin | | | | | | | | | |
| Native | 14 | 3 | | 14.0 | 3.0 | 0 | | | |
| Guanidinated | 0.1 | 3.0 | 13.9 | | | | 0.1 | 3.0 | 14.2 |
| 4. Chymotrypsinogen-A | | | | | | | | | |
| Native | 14 | 4 | | 14.1 | 4.0 | 0 | | | |
| Guanidinated | 0.1 | 4.0 | 14.9 | | | | 0.1 | 3.9 | 13.9 |
| 5. Ovalbumin | | | | | | | | | |
| Native | 20 | 15 | | 20.3 | 15.0 | 0 | | | |
| Guanidinated | 1.8 | 15.1 | 18.2 | | | | 1.6 | 14.9 | 18.3 |
| 6. Bovine Serum Albumin | | | | | | | | | |
| Native | 59 | 23 | | 59.0 | 23.9 | 0 | | | |
| Guanidinated | 3.2 | 22.9 | 56.2 | | | | 3.9 | 23.2 | 55.0 |
| 7. Chymotrypsinogen | 14 | 4 | | 14.0 | 4.0 | 0 | | | |
| Elastase | 3 | 12 | | | | | 3.0 | 12.1 | 0 |

[a]Values expressed as number per protein molecule
[b]Published values for native proteins; determined values for guanidinated proteins
[c]Pairs of protein passed through the barbiturate matrix
[d]Abbreviation used: Har, homoarginine Included in Table 1 are the analyses of two other studies using the native and guanidinated components of chymotrypsin and ovalbumin (elution profiles not shown). In each case the peak fractions of the chromatographic entities represent completely separated components. Each of the native proteins binds to the column and in each case the guanidinated derivative has a much higher affinity. Despite the negatively charged nature of the matrix, the matrix binds proteins as anionic as bovine serum albumin α-lactalbumin and ovalbumin, and also 1,6-diaminohexane, a homolog of the decarboxylated product of lysine were studied individually.

FIG. 8 illustrates the results of chromatography at pH 8.5 (top row) and 6.5 (bottom row) through barbiturate derivative of Sepharose 4B of 1, 6-diaminohexane (left panels), agmatine (middle panels), and histamine (right panels) in 1 mM Tris chloride; 1.5 to 2.5 mg of amine was applied in each run. Hexanediamine binds in neither instance, indicating the weakness of simple electrostatic attraction with this matrix. Agmatine binds at both pH values whereas histamine binds only at pH 6.5.

To confirm the weakness of the effect of the amino group, 2-acetamidoethyl-guanidine, was passed through the same column at pH 6.5 and its elution was followed qualitatively by the Sakaguchi reaction. The pattern was identical to that of agmatine. Thus binding in the latter case was virtually limited to that of the guanidino group.

The reaction with O-methylisourea is one of the more specific forms of chemical modification of proteins. Restricted to the conversion of lysine residues to homoarginine, it has only modest effects on the activity of proteins unless there is a lysine at the active site, as in pancreatic ribonuclease. It is therefore, reasonable to attribute the increased binding by barbiturate-Sepharose to the added guanidino groups.

The above experiments indicate the selective high affinity of barbiturate anions on an insoluble matrix for the guanidino groups of homoarginine and arginine and the imidazole group of histidine residues in different proteins. The affinity of the barbiturate for the residues reflects a combination of pi-electron and electro-static effects.

The success of the present study is dependent upon the surface exposure of the guanidino groups of homoarginine and arginine residues and of the imidazole groups of histidine. The fact that arginine is the most hydrophilic of groups on the surface of a protein and that this group is at some distance from the backbone of the protein permits the approach of a barbiturate group to form easily the stacking interaction, where the geometry would be more restrictive than that seen with a simple electrostatic bond. In contrast, histidine residues may be buried or fully or partially exposed. These features will determine the degree of accessibility to the matrix. The matrix of the present invention may also have hydrophobic interactions that contribute to the binding of proteins in view of the akyl groups attached to carbon-5 of the barbiturate ring. However, the differences in affinities of the proteins studied rests primarily upon the combined pi-electron and electrostatic interactions.

Pursuant to this embodiment of the present invention, native cationic proteins can be separable in two ways by the barbiturate matrix of the present invention. At pH values of approximately 8 or greater, separation can occur by differences in arginine content. At pH values of approximately 7 and lower, separation can occur because of the sums of differences in arginine and histidine content. Unless there is a high arginine content, the anionic proteins can be separated largely on the latter basis only. Finally, because of the repelling effects of the α-carboxyl group, C-terminal arginine and histidine residues will probably contribute very little to binding.

The present invention provides means for providing a second dimension to the anionic exchanger of the present invention that is based on pi-electron and electrostatic interactions. In this regard, it should be noted that due to the widely dispersed charged state amongst the several electronegative atoms of the barbiturate ring, it is a poor group for simple electrostatic interactions with amino groups. Pursuant to an embodiment of the present invention, an anionic ligand can be selected where the pi electron distribution is similar, but because of fewer electronegative atoms, the charge is more focussed. An example of such an anionic ligand is tyramine coupled by its amino group to a neutral matrix.

The pKa of the phenolic group can be reduced with only modest effects on the electrostatic effect by adding electron-withdrawing groups at both positions ortho to the phenolic hydroxyl group. For instance, with dibromotyramine, the pKa of the phenolic group should be about 6.8. However, other electron-withdrawing groups can be utilized and accordingly, the anionic ligand can be, by way of example, difluorotyramine, dichlorotyramine, diiodotyramine, and dinitrotyramine.

By using a more focussed charge, it is possible to provide a second dimension to the anionic exchanger. The second dimension provides a further separation of proteins.

The present invention provides means for providing a third dimension to the anionic exchanger of the present invention. A third dimension is provided in that, due to the leash length and components of the ligand, the proteins to be separated can be further differentiated. Because the binding, for the anionic exchanger, of histidine or arginine residues to the matrices is through a stacking interaction, the geometry of that interaction is very restrictive. Furthermore, because the amino acid residues have varying degrees of accessibility to the surface of the proteins, especially in the case of histidine, the amino acid residues have varying degrees of accessibility to the ligands. Accordingly, in contrast to the case of simple ion-exchange chromatography, the length of the leash connecting the ligand to the matrix is important. The leash length can be varied to generate different chromatographic elution patterns. Separations can be created by varying the degree of accessibility of the residues to the ligand.

In an embodiment, the anionic exchanger includes a paranitrophenol. In this embodiment, the exchanger has the structure:

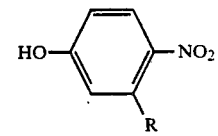

wherein R can be any leash.

As set forth above, in one embodiment of the method of the present invention, an anionic exchanger is utilized to separate proteins based on their arginine and histidine content and provides three separate dimensions for so separating. The present invention also provides a cationic exchanger that will allow the separation of amino acid residues having a negative charge and pi-electron. In this regard, the cationic matrix allows the separation of proteins based on their tyrosine amino acid residues and aspartate and glutamate amino acid residues.

In an embodiment, a cationic matrix is provided synthesized with pi-electrons, for example (β-guanidinoethyl) carbamylmethyl-cellulose, to separate proteins on the basis of an affinity for tyrosine residues in addition to the expected simple electrostatic affinities for the carboxyl residues of aspartic and glutamic acid residues. Despite a pKa of between 9.5 to 10 for the phenol group, the affinity of the matrix is sufficiently strong that it will bind N-acetyltyramine even at pH 8. At this pH, both anionic and cationic proteins show binding.

Following the principles set forth above with respect to the barbiturate matrix, positively charged matrices with expanded pi electron groups in a greater dispersion of electronegative atoms should have an equal or higher affinity for tyrosine residues and a lower affinity for aspartic and glutamic acid residues than that demonstrated by GECM-cellulose. Examples of these matrices include N(β-biguanidoethyl)-carbamylmethyl-cellulose (BGECM)-cellulose and N(β-isomelaminoethyl)-carbamethyl-cellulose.

By way of example, and not limitation, experimental procedures utilizing the cationic matrix possessing pi electrons will now be set forth.

The experiments set forth below demonstrate that a cationic matrix possessing pi electrons, can interact with tyrosine, a component with pi electrons that is anionic at high pH. Specifically, the experiments set forth below demonstrate that a cationic matrix with pi-electrons has a special affinity for the phenolate anion of the tyrosine residue. To this end, a guanidine-containing matrix was synthesized.

The following chemicals and components were utilized in the following experimental procedure Bovine chymotrypsinogen, ribonuclease, tryptamine, ovalbumin, bovine serum albumin, and bis(2-hydroxyethyl)iminotris(hydroxymethyl)methane obtained from Sigma. Tyramine hydrochloride, 1-(3-dimethylaminopropyl)-3-ethyl-carbodiimide, and N-acetylethylenediamine obtained from Aldrich. Acetic anhydride obtained from Mallinckrodt. Tyrosine and phenylethylamine obtained from Calbiochem. Preswollen microgranular CM- and DEAE-cellulose (Whatman CM- and DE-52) obtained from H. Reeve Angel. Dowex-50 4x, 200 to 400 mesh, obtained from BioRad. Phenylacetic acid obtained from Eastman. All other chemicals that were utilized were of the highest purity available.

As set forth below, N(β-guanidinoethyl)carbamylmethylcellulose was synthesized as follows:

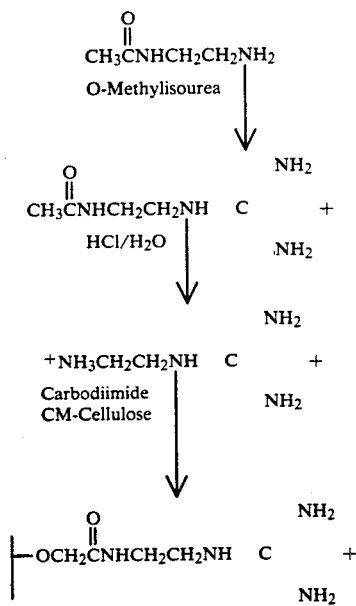

Synthesis of aminoethylguanidine

N-Acetylethylenediamine (15 g) was mixed with O-methylisourea (47 g) in 60 ml of $H_2O$, pH 10.5, for five days at 23° C. Spot tests with minhydrin were performed. If the spot test was positive, acetic anhydide was added to block all residual free amino groups. Thereafter, the solution was passed through a Dowex-50 column (6×15 cm). After a period of flow with $H_2O$, N(α-guanidino)acetamidoethane was eluted with 6M HCl and followed with a qualitative spot test of samples by the Sakaguchi reaction. Positive-testing fractions were hydrolyzed by heating in a reflux apparatus for approximately 16 hours.

The product, aminoethylguanidine, was evaporated to dryness and was dissolved in $H_2O$, neutralized with 10M NaOH and passed through a CM-cellulose column which was eluted with 1M NaCl after a period of flow with $H_2O$. Fractions containing the product showed a correspondence of ninhydrin and Sakaguchi reactions and were pooled and evaporated to dryness by heating. The residue was placed in hot ethanol, which dissolved the aminoethylguanidine. The solid NaCl cake was removed by filtration. The filtrate was cooled and left overnight at 23° C., yielding crystals of aminoethylguanidine.

Synthesis of GECM-cellulose

CM-cellulose (10 g) was washed with $H_2O$ and mixed well with 8.75 g of aminoethylguanidine in 20 ml of $H_2O$. Carbodiimide (9.6 gm) was dissolved in 10 ml of $H_2O$. The solutions were adjusted to a pH 5.5 with 1M HCl and 1M NaOH, respectively. Thereafter the carbodiimide solution was added in three aliquots with continuous adjustments with dilute HCl to maintain the pH at 5.5. After an overnight reaction in a shaker at 23° C., the matrix was washed with $H_2O$.

Phenylethylamine, p-methoxyphenylethylamine, tyramine, and tryptamine were acelylated with acetic anhydride to yield the N-acetylated products. In the case of the tyramine product, reaction with an equal volume of 2M hydroxylamine pH 7.5 was carried out for 10 minutes to remove O-acetyl groups. All products were passed through a Sephadex G-25 column (1.5×35 cm) which retarded the aromatic compounds and made them ready for ion-exchange chromatography. Between approximately 1to about 5 mg of each product was applied in each run.

For the experiments set forth below, all chromatography through cellulose derivatives was done at 23° C. in columns of 0.8 ×9 cm; the buffer was 5 mM tris-HCl unless otherwise indicated. Fractions of 2 ml were collected at a flow rate of one ml/min. After a period of flow with initial buffer, each column was eluted with a linear gradient formed from 30 ml each of starting buffer and the same buffer containing 1M NaCl. Between approximately 1to about 5 mg of each protein was applied in each run. To distinguish between ribonuclease and chymotrypsinogen in FIG. 13, advantage was taken of the absence of tryptophan in the former protein and the presence of seven such residues in chymotrypsinogen. Thus, a low ratio of absorbance at 298 and 280 nm indicated the presence of ribonuclease whereas a higher ratio indicated the presence of chymotrypsinogen.

Previous studies with guanidine-containing matrices involved the conversion of aminoethylcellulose, by reaction with O-methylisourea, to the guanidino derivative. Because that procedure could leave a few unreacted amino groups that could confuse the interpretation of the experiments, GECM-cellulose was synthesized to avoid this complication.

Figure 9A:
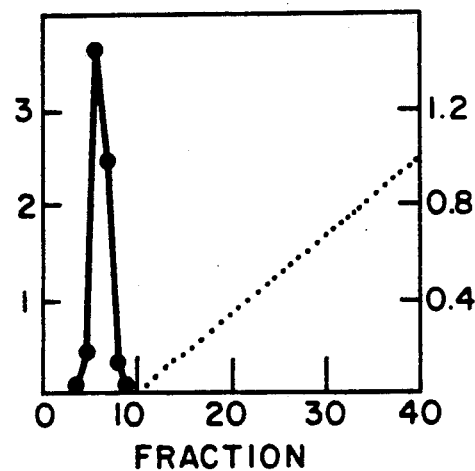
Figure 9B:
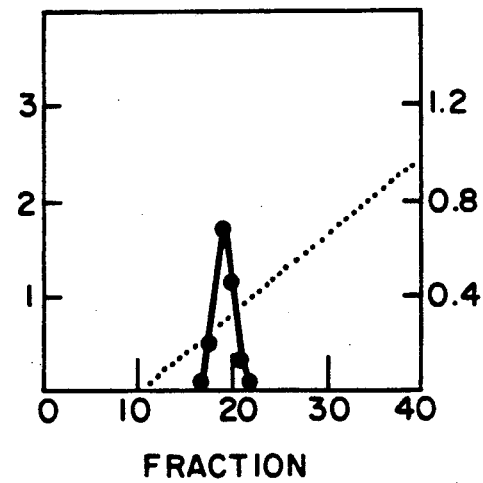
Figure 10A:
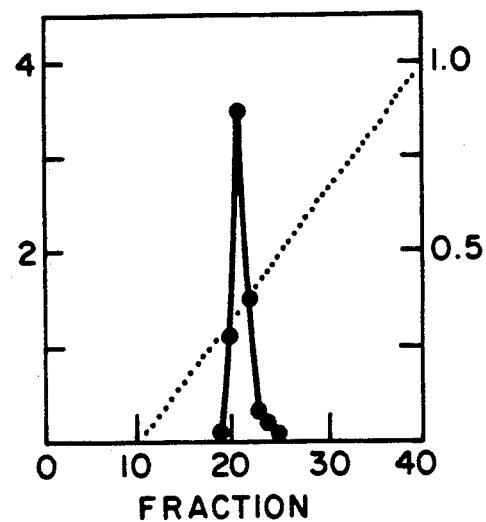
Figure 10B:
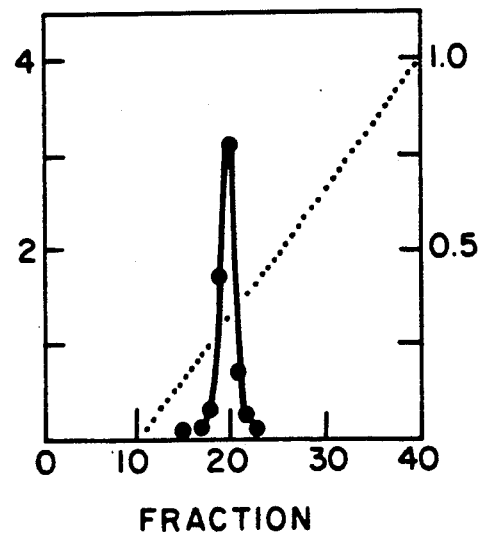
Figure 12A:
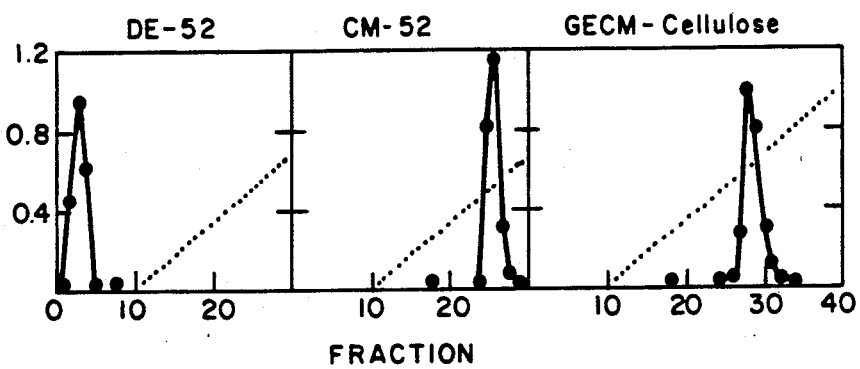
Figure 12B:
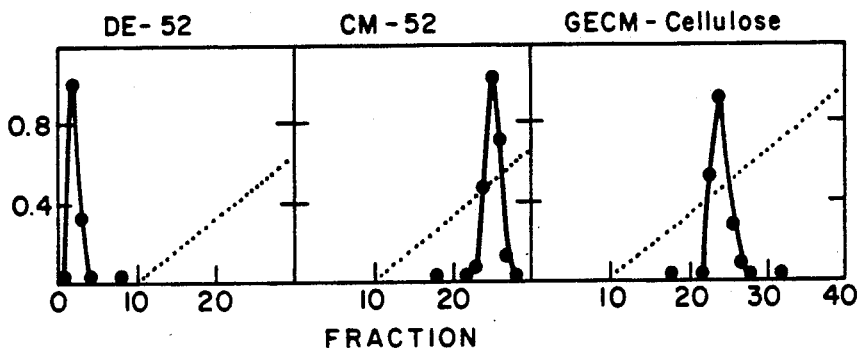
Figure 12C:
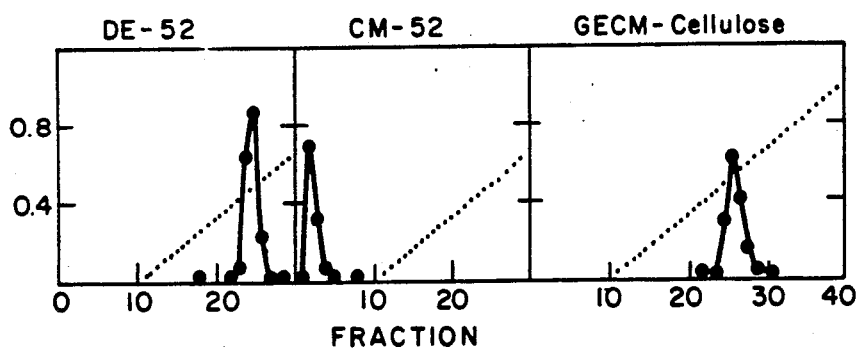
Figure 12D:
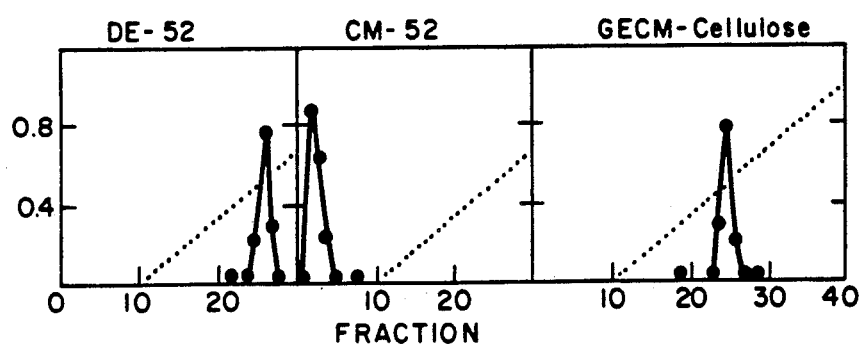

FIG. 9 illustrates the elution patterns of tyramine (upper panel) and tyrosine (lower panel) at pH.8 through GECM-cellulose. As illustrated, tyramine binds weakly, eluting completely before the application of a salt gradient whereas tyrosine shows significant binding. Phenylacetic acid binds equally well to DEAE- and GECM-celluloses (See FIG. 10; DEAE-cellulose (upper panel) and GECM-cellulose (lower panel)). Furthermore, the binding to the latter matrix is similar to that of tyrosine, suggesting an approximate equivalence in binding that is due entirely to the carboxyl groups.

Based on these results, it might be concluded that a combined electrostatic and pi-electron interaction between guanidinium and phenolate groups was unlikely. However, the studies set forth above for the interaction of the barbiturate-containing matrix with imidazole and guanidinium groups showed 1that the α-carboxyl groups of histidine and arginine were sufficiently strong to repel the stacking interaction with the barbiturate anion. This effect was avoided with model compounds without the α-carboxyl group.

Accordingly, an analogous argument was considered that the α-amino group of tyrosine and the related amino group of tyramine could repel a stacking interaction of the guanidinium ion with the phenolate group. Therefore, further studies were conducted with N-acetyltyramine. FIG. 11 illustrates the chromatography of N-acetyltyramine through DEAE-cellulose (panel A) and GECM-cellulose (panels B through E) at the pH values indicated by the numbers within each panel. The buffer in panels D and E was 5 mM bis-Tris. As illustrated, there is no binding at pH 8 with DEAE-cellulose, this is expected in view of the almost fully protonated state of the phenolic group at this pH. In contrast, substantial binding occurs with GECM-cellulose at this pH. Binding is tighter at a pH of 10, very modest at a pH of 7, and absent at a pH of 6.5, indicating a pH dependence. That this binding can be ascribed to the phenolic group was confirmed by showing that neither 2-(phenyl)acetamidoethane nor 2-(4-methoxyphenyl)acetamidoethane showed any binding. The substantial binding at a pH of 8 represents a high affinity of the phenolate anion since N-acetyltyramine is still strongly bound at about 1.5 pH units below the pKa value of the phenolic group. In addition, it was shown that acetylated tryptamine did not bind.

Using this information, a panel of two anionic and two cationic proteins was analyzed. FIG. 12 illustrates the chromatography of chymotrypsinogen-A (row a), ribonuclease (row b), bovine serum albumin (row c), and ovalbumin (row d), through the indicated cellulose matrices. As illustrated, these proteins showed the appropriate affinities for either CM- or DEAE-cellulose at a pH of 8. However, at this pH, all four proteins bind to GECM-cellulose.

Figure 13A:
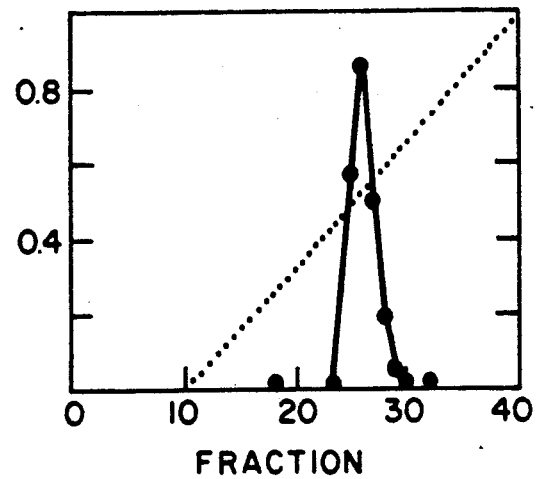
FIG. 13 illustrates the elution patterns for a mixture of ribonuclease and chymotrypsinogen-A through CM-cellulose and GECM-cellulose. Y axis-$A_{280}$●—●, and M NaCl
Figure 13B:
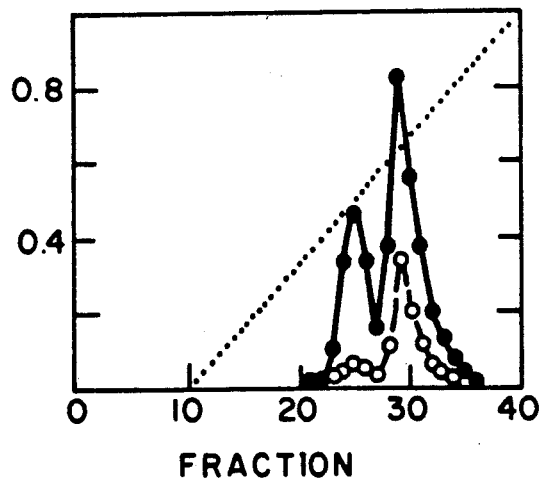

FIG. 13 illustrates the chromatography of a mixture of ribonuclease and chymotrypsinogen-A through CM-cellulose (top panel) and GECM-cellulose (bottom panel). As illustrated, both CM- and GECM-cellulose bound ribonuclease and chymotrypsinogen. However, only GECM-cellulose, a cationic matrix, separated these two cationic proteins, with ribonuclease eluting before chymotrypsinogen. Thus, this matrix separated proteins at pH 8 on the basis of the sum of surface acidic and tyrosine residues.

Because of the repelling effect of the α-amino group, N-terminal tyrosine residues would probably contribute little to protein binding.

Thus, the present invention also provides an anion exchanger that can separate proteins based on the tyrosine amino acid residue. The exchanger also has a lower affinity for aspartate and glutamate residues than that demonstrated by GECM-cellulose.

Like the anionic exchanger, the cationic exchanger can also provide an additional dimension in view of the geometry of binding of tyrosine to the exchanger. Because the geometry of interaction is very restrictive, and these residues having varying degrees of accessibility to the surface of the proteins, especially in the case of tyrosine, they will have varying degrees of accessibility to the ligands. Again, by varying the leash length, different elution patterns and separations can be obtained.

A further cationic exchanger is provided through the substitution on an amino group with an amidino group. This exchanger has the following formula:

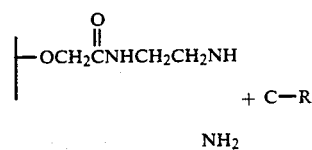

wherein R is an alkane, preferably a small alkane. In a preferred embodiment, R is methyl. Preferably, the exchanger should be created as follows:

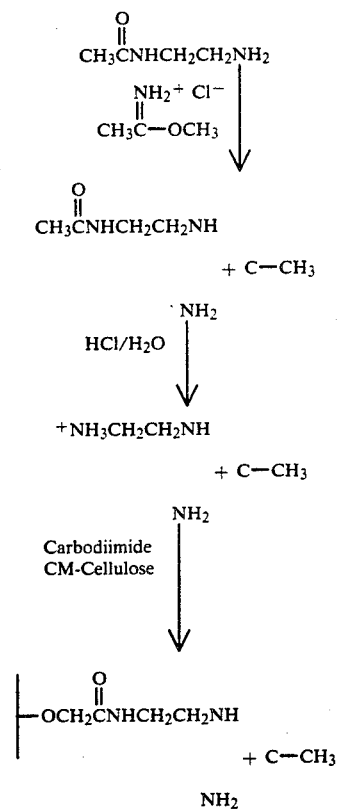

This should bind aspartyl and glutamyl residues more tightly than DEAE, so that it will bind even cationic proteins. A related structure would be an imidazole-containing group.

By way of example, examples of the exchanger will now be given as compared to known techniques of CM-cellulose and DEAE-cellulose.

| Exchanger | pH 8 | pH 6 |
|---|---|---|
| CATIONIC EXCHANGER | | |
| CM | Lys = Arg | Lys = Arg = His |
| Barbiturate | Arg >>> Lys | Arg = His >>> Lys |
| DHT | Arg > Lys | Arg = His > Lys |
| ANIONIC EXCHANGER | | |
| DEAE | Glu = Asp | Glu = Asp |
| GECM | Glu = Asp = Tyr | Glu = Asp |
| BGECM | Tyr > Glu = Asp | |
| AAECM | Tyr >> Glu ≧ Asp | Tyr >> Glu ≧ Asp |

As previously stated, by varying leash length and constituents, further separations can be accomplished.

In use, the cationic exchanger or anionic exchanger can be used in columns to separate proteins. The exchangers can be attached to a matrix such as, for example: cellulose; agarose, dextran; acrylamide; supocel; silica gels; polystyrene; starch; and glass.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A method of separating protein comprising:
contacting said proteins to be separated with a ligand that is cationic, which ligand is attached to a matrix, under conditions that permit pi-electron and electrostatic charge interaction of said ligand with specific amino acid residues of said proteins to be separated; and effecting said separation based on said interaction.

2. The method of claim 1 wherein the ligand includes N($\beta$-guanidinoethyl)carbamylmethyl.

3. The method of claim 1 wherein the ligand includes N($\beta$-biguanidoethyl)-carbamylmethyl.

4. The method of claim 1 wherein the ligand includes (N -isomelaminoethyl)-carbamylmethyl.

5. The method of claim 1 wherein the ligand attached to a matrix by a leash and the leash length is varied to further separate the organic compounds.

6. The method of claim 1 wherein the ligand includes a compound having the formula:

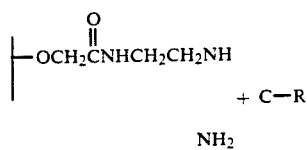

wherein R is an alkane.

7. The method of claim 6 wherein R is methyl.

8. The method of claim 1 wherein the specific amino acid residues are chosen from the group consisting of: arginine; lysine; tyrosine; and glutamate and aspartate.

9. The method of claim 1 wherein the ligand is located in a matrix chosen from the group consisting of cellulose; agarose; dextran; acrylamide; supocel; silia gels; polystyrene; starch; and glass.

10. The method of claim 1 wherein the ligand includes a thiobarbiturate.

11. A method of separating proteins comprising the step of passing the protein through a cationic ligand-linked matrix that separates proteins based on a pi-electron and electrostatic interaction of tyrosine residues in the protein and the ligand.

12. The method of claim 11 wherein the ligand includes N($\beta$-guanidinoethyl)carbamylmethyl.

13. The method of claim 11 wherein the ligand includes N($\beta$-biguanidoethyl)carbamylmethyl.

14. The method of claim 11 wherein the ligand includes N($\beta$-isomelaminoethyl)carbamylmethyl.

15. The method of claim 11 wherein the ligand includes a compound having the formula:

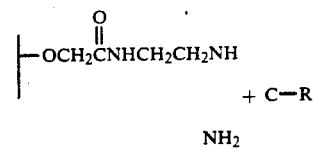

wherein R is an alkane.

16. The method of claim 15 wherein R is methyl.

17. The method of claim 11 including the step of varying a leash length that is secured to the ligand.

* * * * *